United States Patent
Clarkson et al.

(10) Patent No.: US 10,688,025 B2
(45) Date of Patent: Jun. 23, 2020

(54) PERSONAL CLEANSING COMPOSITIONS COMPRISING A CATIONIC POLYMER MIXTURE

(71) Applicant: Conopco, Inc., Englewood Cliffs, NJ (US)

(72) Inventors: Heather Clarkson, Wirral (GB); Jayne Lesley Dawson, Wirral (GB); Cesar Ernesto Mendoza Fernandez, Liverpool (GB); Andrew Malcolm Murray, Neston (GB); Neil Scott Shaw, Warrington (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 70 days.

(21) Appl. No.: 15/770,623

(22) PCT Filed: Oct. 4, 2016

(86) PCT No.: PCT/EP2016/073622
§ 371 (c)(1),
(2) Date: Apr. 24, 2018

(87) PCT Pub. No.: WO2017/071915
PCT Pub. Date: May 4, 2017

(65) Prior Publication Data
US 2019/0060187 A1    Feb. 28, 2019

(30) Foreign Application Priority Data

Oct. 29, 2015   (EP) .................................... 15192185

(51) Int. Cl.
| | | |
|---|---|---|
| C11D 1/02 | (2006.01) |
| A61K 8/11 | (2006.01) |
| A61K 8/46 | (2006.01) |
| A61Q 5/02 | (2006.01) |
| A61K 8/73 | (2006.01) |
| A61K 8/81 | (2006.01) |
| A61Q 19/10 | (2006.01) |
| A61K 8/58 | (2006.01) |
| A61Q 5/12 | (2006.01) |
| A61K 8/89 | (2006.01) |

(52) U.S. Cl.
CPC ................ A61K 8/11 (2013.01); A61K 8/463 (2013.01); A61K 8/466 (2013.01); A61K 8/585 (2013.01); A61K 8/737 (2013.01); A61K 8/8158 (2013.01); A61K 8/89 (2013.01); A61Q 5/02 (2013.01); A61Q 5/12 (2013.01); A61Q 19/10 (2013.01); A61K 2800/412 (2013.01)

(58) Field of Classification Search
CPC ........... C11D 1/02; C11D 3/162; C11D 3/373; C11D 3/50; C11D 3/505; C11D 9/225; C11D 9/44; C11D 9/36
See application file for complete search history.

(56) References Cited

U.S. PATENT DOCUMENTS

| | | |
|---|---|---|
| 2004/0157755 A1 | 8/2004 | Niemiec et al. |
| 2011/0002868 A1 | 1/2011 | Bierganns et al. |
| 2012/0076747 A1 | 5/2012 | Bierganns et al. |
| 2013/0089587 A1 | 4/2013 | Staudigel et al. |
| 2014/0335041 A1* | 11/2014 | Peffly ....................... A61K 8/89 424/70.121 |
| 2015/0096582 A1 | 4/2015 | Stella et al. |
| 2016/0256365 A1* | 9/2016 | Dihora ..................... A61K 8/11 |
| 2016/0310397 A1* | 10/2016 | Johnson ................... A61K 8/58 |
| 2018/0015009 A1* | 1/2018 | Soubiran .................. A23L 2/56 |
| 2018/0021236 A1* | 1/2018 | Snyder .................. A61K 8/585 510/122 |
| 2018/0353398 A1* | 12/2018 | Torres Rivera .......... A61K 8/20 |
| 2019/0192405 A1* | 6/2019 | Zhao ....................... A61K 8/463 |

FOREIGN PATENT DOCUMENTS

| | | |
|---|---|---|
| DE | 102011004122 | 8/2012 |
| WO | WO9963965 | 12/1999 |
| WO | WO03028683 | 4/2003 |
| WO | WO2007065537 | 7/2007 |
| WO | WO2012138696 | 10/2012 |
| WO | WO2012138710 | 10/2012 |
| WO | WO2016177607 | 11/2016 |

OTHER PUBLICATIONS

Written Opinion 2 in PCTEP2016073622, dated Sep. 8, 2017.
Search Report & Written Opinion in PCTEP2016073622, dated Nov. 8, 2016.
Search Report & Written Opinion in EP15192185, dated Feb. 4, 2016.
IPRP2 in PCTEP2016073622, Jan. 30, 2018.

* cited by examiner

*Primary Examiner* — Charles I Boyer
(74) *Attorney, Agent, or Firm* — Foley & Lardner LLP

(57) ABSTRACT

The invention provides a personal cleansing composition comprising, in an aqueous continuous phase: (i) from 5 to 30% by weight of one or more anionic cleansing surfactants; (ii) from 0.1 to 10% by weight of discrete, dispersed droplets of emulsified silicone with a mean diameter (D3,2) of 4 micrometres or less; (iii) from 0.1 to 5% by weight of microcapsules in which a core comprising benefit agent is encapsulated in a polymeric shell, and (iv) from 0.1 to 0.5% by weight of a combination of cationic polymers comprising: (a) at least one cationic polygalactomannan derivative having a mean charge density at pH 7 from 0.2 to 2 meq per gram; and (b) at least one acrylamidopropyltrimonium chloride/acrylamide copolymer having a mean charge density at pH 7 from 1 to 3 meq per gram.

5 Claims, No Drawings

PERSONAL CLEANSING COMPOSITIONS COMPRISING A CATIONIC POLYMER MIXTURE

CROSS-REFERENCE TO RELATED PATENT APPLICATIONS

This application is a national stage entry under 35 U.S.C. § 371 of International Application No. PCT/EP2016/073622, filed Oct. 4, 2016, which claims the benefit and priority under 35 U.S.C. § 119(e) of European Application No. 1519218.5, filed Oct. 29, 2015, the contents of each of which are incorporated by reference into the present disclosure.

FIELD OF THE INVENTION

The present invention relates to personal cleansing compositions such as liquid soaps, body washes and shampoos.

BACKGROUND AND PRIOR ART

In personal cleansing compositions such as liquid soaps, body washes and shampoos, the deposition and delivery of benefit agents are often key drivers of product performance. For example, many of the shampoo products in the market today work to deliver benefits to hair by depositing benefit agents such as fragrance materials, silicones, dyes, and anti-dandruff agents onto the hair during washing.

Various technologies have been employed to enhance the delivery of benefit agents at the desired time. One widely used technology is encapsulation of the benefit agent in a protective coating such as a polymeric material. The polymeric material may protect the benefit agent, such as a fragrance material, from evaporation, reaction, oxidation or otherwise dissipating prior to use.

However, maximizing encapsulate deposition during cleansing is a difficult task since most personal cleansing compositions were designed to carry away particulates from the skin or hair. When encapsulates are washed away, relatively high levels of encapsulated benefit agents may be needed in the composition to deliver the consumer desired benefit.

Accordingly, there is a need for a personal cleansing composition that provides an increased deposition of encapsulated benefit agents onto the hair or skin, without impairing other product attributes such as rheology, sensory and conditioning performance.

The present invention addresses this problem.

SUMMARY OF THE INVENTION

The present invention provides a personal cleansing composition comprising, in an aqueous continuous phase:
(i) from 5 to 30% by weight of one or more anionic cleansing surfactants;
(ii) from 0.1 to 10% by weight of discrete, dispersed droplets of emulsified silicone with a mean diameter (D3,2) of 4 micrometres or less;
(iii) from 0.1 to 5% by weight of microcapsules in which a core comprising benefit agent is encapsulated in a polymeric shell, and
(iv) from 0.1 to 0.5% by weight of a combination of cationic polymers comprising:
(a) at least one cationic polygalactomannan having a mean charge density at pH7 from 0.2 to 2 meq per gram; and
(b) at least one acrylamidopropyltrimonium chloride/acrylamide copolymer having a mean charge density at pH7 from 1 to 3 meq per gram.

DETAILED DESCRIPTION AND PREFERRED EMBODIMENTS

All molecular weights as used herein are weight average molecular weights, unless otherwise specified.

By "aqueous continuous phase" is meant a continuous phase which has water as its basis.

Suitably, the composition of the invention will comprise from about 50 to about 90%, preferably from about 55 to about 85%, more preferably from about 60 to about 85%, most preferably from about 65 to about 83% water (by weight based on the total weight of the composition).

Typical anionic cleansing surfactants (i) for use in the invention include those surface active agents which contain an organic hydrophobic group with from 8 to 14 carbon atoms, preferably from 10 to 14 carbon atoms in their molecular structure; and at least one water-solubilising group which is preferably selected from sulphate, sulphonate, sarcosinate and isethionate.

Specific examples of such anionic cleansing surfactants include ammonium lauryl sulphate, ammonium laureth sulphate, trimethylamine lauryl sulphate, trimethylamine laureth sulphate, triethanolamine lauryl sulphate, trimethylethanolamine laureth sulphate, monoethanolamine lauryl sulphate, monoethanolamine laureth sulphate, diethanolamine lauryl sulphate, diethanolamine laureth sulphate, lauric monoglyceride sodium sulphate, sodium lauryl sulphate, sodium laureth sulphate, potassium lauryl sulphate, potassium laureth sulphate, sodium lauryl sarcosinate, sodium lauroyl sarcosinate, lauryl sarcosine, ammonium cocoyl sulphate, ammonium lauroyl sulphate, sodium cocoyl sulphate, sodium lauryl sulphate, potassium cocoyl sulphate, potassium lauryl sulphate, monoethanolamine cocoyl sulphate, monoethanolamine lauryl sulphate, sodium tridecyl benzene sulphonate, sodium dodecyl benzene sulphonate, sodium cocoyl isethionate and mixtures thereof.

A preferred class of anionic cleansing surfactants for use in the invention are alkyl ether sulphates of general formula:

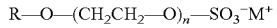

in which R is a straight or branched chain alkyl group having 10 to 14 carbon atoms, n is a number that represents the average degree of ethoxylation and ranges from 1 to 5, preferably from 1 to 3, and M is a alkali metal, ammonium or alkanolammonium cation, preferably sodium, potassium, monoethanolammonium or triethanolammonium, or a mixture thereof.

Specific examples of such preferred anionic surfactants include the sodium, potassium, ammonium or ethanolamine salts of $C_{10}$ to $C_{12}$ alkyl sulphates and $C_{10}$ to $C_{12}$ alkyl ether sulphates (for example sodium lauryl ether sulphate), Mixtures of any of the above described materials may also be used.

In a typical composition according to the invention the level of anionic cleansing surfactant will generally range from 8 to 25%, and preferably ranges from 10 to 16% by weight based on the total weight of the composition.

The aqueous continuous phase of the composition according to the invention preferably also includes one or more amphoteric surfactants, in addition to the anionic cleansing surfactant described above. Suitable amphoteric surfactants are betaines, such as those having the general formula $R(CH_3)_2N^+CH_2COO^-$, where R is an alkyl or alkylamidoalkyl group, the alkyl group preferably having 10 to 16 carbon atoms. Particularly suitable betaines are oleyl betaine, caprylamidopropyl betaine, lauramidopropyl betaine, isostearylamidopropyl betaine, and cocoamidopropyl betaine. Cocoamidopropyl betaine is particularly preferred.

When included, the total level of amphoteric surfactant is preferably from 0.1 to 10%, more preferably from 0.5 to 5%, and most preferably from 1 to 3% by weight based on the total weight of the hair cleansing composition).

Droplets of emulsified silicone (ii) for inclusion in the composition of the invention typically have a mean droplet diameter (D3,2) of 2 micrometres or less. Preferably the mean droplet diameter (D3,2) is 1 micrometre or less, more preferably 0.5 micrometre or less, and most preferably 0.25 micrometre or less.

A suitable method for measuring the mean droplet diameter (D3,2) is by laser light scattering using an instrument such as a Malvern Mastersizer.

Suitable silicones for use in the invention include polydiorganosiloxanes, in particular polydimethylsiloxanes (dimethicones), polydimethyl siloxanes having hydroxyl end groups (dimethiconols), and amino-functional polydimethylsiloxanes (amodimethicones).

Such silicones are preferably non-volatile (with vapour pressure of less than 1000 Pa at 25° C.), and preferably have a molecular weight of greater than 100,000, more preferably greater than 250,000.

Such silicones preferably have a kinematic viscosity of greater than 50,000 cS ($mm^2 \cdot s^{-1}$) and more preferably a kinematic viscosity of greater than 500,000 cS ($mm^2 \cdot s^{-1}$). Silicone kinematic viscosities in the context of this invention are measured at 25° C. and can be measured by means of a glass capillary viscometer as set out further in Dow Corning Corporate Test Method CTM004 Jul. 20, 1970.

Suitable silicones for use in the invention are available as pre-formed silicone emulsions from suppliers such as Dow Corning and GE Silicones. The use of such pre-formed silicone emulsions is preferred for ease of processing and control of silicone particle size. Such pre-formed silicone emulsions will typically additionally comprise a suitable emulsifier, and may be prepared by a chemical emulsification process such as emulsion polymerisation, or by mechanical emulsification using a high shear mixer. Pre-formed silicone emulsions having a mean droplet diameter (D3,2) of less than 0.15 micrometres are generally termed microemulsions.

Examples of suitable pre-formed silicone emulsions include emulsions DC2-1766, DC2-1784, DC-1785, DC-1786, DC-1788, DC-1310, DC-7123 and microemulsions DC2-1865 and DC2-1870, all available from Dow Corning. These are all emulsions/microemulsions of dimethiconol. Also suitable are amodimethicone emulsions such as DC939 (from Dow Corning) and SME253 (from GE Silicones).

Mixtures of any of the above described silicone emulsions may also be used.

In a typical composition according to the invention the level of silicone (per se as active ingredient) will generally range from 1 to 8%, and preferably ranges from 2 to 7.5% by weight based on the total weight of the composition.

The composition of the invention may suitably include at least one inorganic electrolyte. The inorganic electrolyte may be used to help provide viscosity to the composition.

The viscosity of the composition suitably ranges from 3,000 to 10,000 mPa·s, preferably from 4,000 to 8,000 mPa·s, more preferably from 5,000 to 7,000 mPa·s when measured using a Brookfield V2 viscometer (spindle RTV5, 1 minute, 20 rpm) at 30° C.

Suitable inorganic electrolytes include metal chlorides (such as sodium chloride, potassium chloride, calcium chloride, magnesium chloride, zinc chloride, ferric chloride and aluminium chloride) and metal sulphates (such as sodium sulphate and magnesium sulphate).

Examples of preferred inorganic electrolytes for use in the invention include sodium chloride, potassium chloride, magnesium sulphate and mixtures thereof.

The composition of the invention comprises microcapsules (iii) in which a core comprising benefit agent is encapsulated in a polymeric shell.

The term "benefit agent" in the context of this invention includes materials which can provide a benefit to the hair and/or the scalp and/or the skin (preferably the hair and/or the scalp) as well as those materials which are beneficially incorporated into personal cleansing compositions, such as aesthetic agents.

The benefit agent of the core of the microcapsule may suitably be selected from perfumes, cosmetic active ingredients such as antimicrobial agents, antidandruff agents, moisturisers, conditioning agents, sunscreening agents, physiological coolants and emollient oils; and mixtures thereof.

Preferably the benefit agent of the core of the microcapsule is selected from perfumes. A perfume normally consists of a mixture of a number of perfume materials, each of which has an odour or fragrance. The number of perfume materials in a perfume is typically 10 or more. The range of fragrant materials used in perfumery is very wide; the materials come from a variety of chemical classes, but in general are water-insoluble oils. In many instances, the molecular weight of a perfume material is in excess of 150, but does not exceed 300.

Examples of perfume materials for use in the invention include geraniol, geranyl acetate, linalol, linalyl acetate, tetrahydrolinalol, citronellol, citronellyl acetate, dihydromyrcenol, dihydromyrcenyl acetate, tetrahydromyrcenol, terpineol, terpinyl acetate, nopyl acetate, 2-phenyl-ethanol, 2-penylethyl acetate, benzyl alcohol, benzyl acetate, benzyl salicylate, styrallyl acetate, benzyl benzoate, amyl salicylate, dimethylbenzyl-carbinol, trichloromethylphenyl-carbinyl acetate, p-tert-butylcyclohexyl acetate, isononyl acetate, vetiveryl acetate, vetiverol, α-hexylcinnamaldehyde, 2-methyl-3-p-tert-butylpheyl)propanal, 2-methyl-3-(p-isopropylphenyl)propanal, 2-(p-tert-butylpheyl)propanal, 2,4-dimethyl-cyclohex-3-enyl-carboxaldehyde, tricyclodecenyl acetate, tricyclodecenyl propionate, 4-(4-hydroxy-4-methylpentyl)-3-cyclohexenecarboxyaldehyde, 4-(4-methyl-3-pentenyl)-3-cyclohexenecarboxaldehyde, 4-acetoxy-3-pentyl-tetrahydropyran, 3-carboxymethyl-2-pentylcyclopentane, 2-n-heptylcyclopentanone, 3-methyl-2-pentyl-2-cyclopentenone, n-decanal, n-dodecanal, 9-decenol-1, phenoxyethyl isobutyrate, phenyl-acetaldehyde dimethyl-acetal, phenylacetaldehyde diethylacetal, geranyl nitrile, citronellyl nitrile, cedryl acetate, 3-isocamphylcyclohexanol, cedryl methyl ether, isolongifolanone, aubepine nitrile, aubepine, heliotropin, coumarin, eugenol, vanillin, diphenyl oxide, hydroxycitronellal, ionones, methylionones, isomethylionones, irones, cis-3-hexenol and esters thereof, indan musks, tetralin musks, isochroman musks, macrocyclic ketones, macrolactone musks, ethylene brassylate and mixtures thereof.

Optional further materials which may be included in the core of the microcapsule include dyes, pigments and preservatives.

The polymeric shell of the microcapsule may be prepared using methods known to those skilled in the art such as coacervation, interfacial polymerisation and polycondensation.

The process of coacervation typically involves encapsulation of a generally water-insoluble material by the precipitation of colloidal material(s) onto the surface of droplets of the material. Coacervation may be simple e.g. using one colloid such as gelatin, or complex where two or possibly more colloids of opposite charge, such as gelatin and gum arabic or gelatin and carboxymethyl cellulose, are used under carefully controlled conditions of pH, temperature and concentration.

Interfacial polymerisation produces encapsulated shells from the reaction of at least one oil-soluble wall forming material present in the oil phase with at least one water-soluble wall forming material present in the aqueous phase. A polymerisation reaction between the two wall-forming materials occurs resulting in the formation of covalent bonds at the interface of the oil and aqueous phases to form the capsule wall. An example of a shell capsule produced by this method is a polyurethane capsule.

Polycondensation involves forming a dispersion or emulsion of water-insoluble material (e.g. perfume) in an aqueous solution of precondensate of polymeric materials under appropriate conditions of agitation to produce capsules of a desired size, and adjusting the reaction conditions to cause condensation of the precondensate by acid catalysis, resulting in the condensate separating from solution and surrounding the dispersed water-insoluble material to produce a coherent film and the desired microcapsules.

A preferred method for forming microcapsules for use in the invention is polycondensation, typically to produce aminoplast encapsulates. Aminoplast resins are the reaction products of one or more amines with one or more aldehydes. Examples of suitable amines include urea, thiourea, melamine and its derivatives, benzoguanamine and acetoguanamine and combinations of amines.

Preferably the polymeric shell of the microcapsule is an aminoplast resin selected from melamine formaldehyde, urea formaldehyde, melamine glyoxal and polyurea formed by reaction of polyisocyanates and polyamines. The most preferred polymeric shell is selected from melamine glyoxal and polyurea.

Advantageously the polymeric shell comprises at most 20 wt % of the weight of the microcapsules.

By modifying process conditions microcapsules of a desired size can be produced in known manner. The microcapsules typically have a mean diameter in the range 1 to 500 microns, preferably 1 to 300 microns, more preferably 1 to 50 microns and most preferably 1 to 10 microns. If necessary, the microcapsules as initially produced may be filtered or screened to produce a product of greater size uniformity.

In a typical composition according to the invention the level of microcapsules (iii) will generally range from 0.2 to 2%, and preferably ranges from 0.5 to 1.5% by weight based on the total weight of the composition.

The composition of the invention comprises, inter alia, a combination of cationic polymers (iv) comprising:
(a) at least one cationic polygalactomannan having a mean charge density at pH7 from 0.2 to 2 meq per gram; and
(b) at least one acrylamidopropyltrimonium chloride/acrylamide copolymer having a mean charge density at pH7 from 1 to 3 meq per gram.

The term "charge density" in the context of this invention refers to the ratio of the number of positive charges on a monomeric unit of which a polymer is comprised to the molecular weight of the monomeric unit. The charge density multiplied by the polymer molecular weight determines the number of positively charged sites on a given polymer chain.

The polygalactomannans are polysaccharides composed principally of galactose and mannose units and are usually found in the endosperm of leguminous seeds, such as guar, locust bean, honey locust, flame tree, and the like. Guar flour is composed mostly of a galactomannan which is essentially a straight chain mannan with single membered galactose branches. The mannose units are linked in a 1-4-β-glycosidic linkage and the galactose branching takes place by means of a 1-6 linkage on alternate mannose units. The ratio of galactose to mannose in the guar polymer is therefore one to two.

Suitable cationic polygalactomannans (a) for use in the invention include polygalactomannans, such as guars, and polygalactomannan derivatives, such as hydroxyalkyl guars (for example hydroxyethyl guars or hydroxypropyl guars), that have been cationically modified by chemical reaction with one or more derivatizing agents.

Derivatizing agents typically contain a reactive functional group, such as an epoxy group, a halide group, an ester group, an anhydride group or an ethylenically unsaturated group, and at least one cationic group such as a cationic nitrogen group, more typically a quaternary ammonium group. The derivatization reaction typically introduces lateral cationic groups on the polygalactomannan backbone, generally linked via ether bonds in which the oxygen atom corresponds to hydroxyl groups on the polygalactomannan backbone which have reacted.

Preferred cationic polygalactomannans (a) for use in the invention include guar hydroxypropyltrimethylammonium chlorides.

Guar hydroxypropyltrimethylammonium chlorides for use in the invention are generally comprised of a nonionic guar gum backbone that is functionalized with ether-linked 2-hydroxypropyltrimethylammonium chloride groups, and are typically prepared by the reaction of guar gum with N-(3-chloro-2-hydroxypropyl) trimethylammonium chloride.

Cationic polygalactomannans (a) for use in the invention (preferably guar hydroxypropyltrimethylammonium chlorides) generally have an average molecular weight (weight average molecular mass (Mw) determined by size exclusion chromatography) in the range 500,000 to 3 million g/mol, more preferably 800,000 to 2.5 million g/mol.

Cationic polygalactomannans (a) for use in the invention (preferably guar hydroxypropyltrimethylammonium chlorides) generally have a charge density ranging from 0.5 to 1.8 meq/g.

The cationic charge density of the polymer is suitably determined via the Kjeldahl method as described in the US Pharmacopoeia under chemical tests for nitrogen determination.

Specific examples of preferred cationic polygalactomannans (a) are guar hydroxypropyltrimonium chlorides having a cationic charge density from 0.5 to 1.1 meq/g.

Also suitable are mixtures of cationic polygalactomannans (a) in which one has a cationic charge density from 0.5 to 1.1 meq/g, and one has a cationic charge density from 1.1 to 1.8 meq per gram.

]Specific examples of preferred mixtures of cationic polygalactomannans (a) are mixtures of guar hydroxypropyltrimonium chlorides in which one has a cationic charge density from 0.5 to 1.1 meq/g, and one has a cationic charge density from 1.1 to 1.8 meq per gram.

Cationic polygalactomannans (a) for use in the invention are commercially available from Rhodia as JAGUAR @ C13S, JAGUAR @ C14 and JAGUAR @ C17.

In a typical composition according to the invention the level of cationic polygalactomannans (a) will generally range from 0.05 to 0.25%, and preferably ranges from 0.15 to 0.2% by weight based on the total weight of the composition.

Acrylamidopropyltrimonium chloride/acrylamide copolymers (b) for use in the invention generally have an average molecular weight (weight average molecular mass (Mw) determined by size exclusion chromatography) in the range 500,000 to 2 million g/mol, preferably 800,000 to 1.5 million g/mol.

Acrylamidopropyltrimonium chloride/acrylamide copolymers (b) for use in the invention generally have a charge density ranging from 1 to 2.5 meq/g, preferably from 1.5 to 2.2 meq/g.

Acrylamidopropyltrimonium chloride/acrylamide copolymers (b) for use in the invention are commercially available from Ashland as N-Hance® SP-100.

In a typical composition according to the invention the level of acrylamidopropyltrimonium chloride/acrylamide copolymers (b) will generally range from 0.05 to 0.25%, and preferably ranges from 0.05 to 0.1% by weight based on the total weight of the composition.

The level of the combination of cationic polymers (iv) in the composition will generally range from 0.15 to 0.4%, and preferably ranges from 0.2 to 0.3% by weight based on the total weight of the composition.

The weight ratio of cationic polymer (a) to cationic polymer (b) in the composition will generally range from 4:1 to 1:1, and preferably ranges from 3:1 to 1:1.

A composition of the invention may contain further optional ingredients to enhance performance and/or consumer acceptability. Examples of such ingredients include fragrance, dyes and pigments, pH adjusting agents and preservatives or antimicrobials. Each of these ingredients will be present in an amount effective to accomplish its purpose. Generally these optional ingredients are included individually at a level of up to 5% by weight based on the total weight of the composition.

The pH of the composition of the invention preferably ranges from 4 to 7, more preferably from 5.5 to 6.5.

Mode of Use

The composition of the invention is primarily intended for topical application to the body, preferably the hair and scalp.

Most preferably the composition of the invention is topically applied to the hair and then massaged into the hair and scalp. The composition is then rinsed off the hair and scalp with water prior to drying the hair.

The invention will be further illustrated by the following, non-limiting Examples, in which all percentages quoted are by weight based on total weight unless otherwise stated.

EXAMPLES

Hair cleansing shampoo formulations were prepared, having ingredients as shown in Table 1 below. Examples 1 to 4 represent formulations according to the invention. Examples A to D represent comparative examples (not according to the invention).

TABLE 1

| Ingredient | Example A | Example B | Example C | Example 1 |
| --- | --- | --- | --- | --- |
| | | wt % (active ingredient) | | |
| Sodium laureth sulfate (2EO) | 12 | 12 | 12 | 12 |
| Cocamidopropyl betaine | 1.6 | 1.6 | 1.6 | 1.6 |
| Carbomer | 0.4 | 0.4 | 0.4 | 0.4 |
| JAGUAR ® C14S | 0.2 | 0.15 | — | 0.15 |
| JAGUAR ® C17 | — | 0.05 | 0..2 | — |
| N-Hance ® SP-100 | — | — | — | 0.05 |
| Silicone (DOW CORNING ® 1788 Emulsion) | 5 | 5 | 5 | 5 |
| Encapsulated perfume (ex Firmenich) | 1 | 1 | 1 | 1 |
| Polypropylene glycol | 0.25 | 0.25 | 0.25 | 0.25 |
| Water, minors | q.s. to 100 | q.s. to 100 | q.s. to 100 | q.s. to 100 |

| Ingredient | Example 2 | Example 3 | Example 4 | Example D |
| --- | --- | --- | --- | --- |
| | | wt % (active ingredient) | | |
| Sodium laureth sulfate (2EO) | 12 | 12 | 12 | 12 |
| Cocamidopropyl betaine | 1.6 | 1.6 | 1.6 | 1.6 |
| Carbomer | 0.4 | 0.4 | 0.4 | 0.4 |
| JAGUAR ® C14S | 0.1 | 0.1 | 0.15 | — |
| JAGUAR ® C17 | 0.05 | — | 0.05 | — |
| N-Hance ® SP-100 | 0.05 | 0.1 | 0.1 | 0.2 |
| Silicone (DOW CORNING ® 1788 Emulsion) | 5 | 5 | 5 | 5 |
| Encapsulated perfume (ex Firmenich) | 1 | 1 | 1 | 1 |
| Polypropylene glycol | 0.25 | 0.25 | 0.25 | 0.25 |
| Water, minors | q.s. to 100 | q.s. to 100 | q.s. to 100 | q.s. to 100 |

The formulations were evaluated by measuring both silicone deposition and encapsulated perfume (encap) deposition on hair. Silicone deposition and encapsulated fragrance deposition were measured by XRF. 0.25 g test formulation was applied to 2.5 g/6" switches of wet hair. The formulation was massaged on hair for 30 seconds followed by rinsing with warm water for 30 seconds. The treatment was repeated once. Five replicas were produced for each formulation. The results are shown in Table 2 below.

TABLE 2

| Example | Silicone deposition (ppm) | Std Dev | Encap deposition eff (%) | Std Dev |
| --- | --- | --- | --- | --- |
| A | 1385 | 163 | 35 | 0.18 |
| B | 1871 | 830 | 24 | 0.16 |

TABLE 2-continued

| Example | Silicone deposition (ppm) | Std Dev | Encap deposition eff (%) | Std Dev |
|---|---|---|---|---|
| C | 1781 | 850 | 14 | 0.02 |
| 1 | 3448 | 1658 | 23 | 0.14 |
| 2 | 3460 | 1130 | 25 | 0.05 |
| 3 | 3556 | 1635 | 22 | 0.01 |
| 4 | 3003 | 2778 | 19 | 0.06 |
| D | 2837 | 3054 | 1 | 0.01 |

It can be seen from the results that Examples 1 to 4 according to the invention provide effective deposition of both silicone and encapsulated perfume. By contrast, comparative Examples A to D demonstrate either poor silicone deposition or poor encapsulated perfume deposition, or both. The pattern of deposition on the hair from the comparative examples is also observed to be relatively patchy and uneven, as evidenced by the standard deviation values.

The invention claimed is:

1. A personal cleansing composition comprising, in an aqueous continuous phase:
   (i) from 5 to 30% by weight of one or more anionic cleansing surfactants;
   (ii) from 0.1 to 10% by weight of discrete, dispersed droplets of emulsified silicone with a mean diameter (D3,2) of 4 micrometres or less;
   (iii) from 0.1 to 5% by weight of microcapsules in which a core comprising benefit agent is encapsulated in a polymeric shell, and
   (iv) from 0.1 to 0.5% by weight of a combination of cationic polymers comprising:
      (a) at least one cationic polygalactomannan having a mean charge density at pH 7 from 0.2 to 2 meq per gram comprising guar hydroxypropyltrimonium chlorides having a cationic charge density from 0.5 to 1.1 meq per gram; and
      (b) at least one acrylamidopropyltrimonium chloride/acrylamide copolymer having a mean charge density at pH from 1 to 3 meq per gram, wherein the weight ratio of cationic polymer (a) to cationic polymer (b) in the composition ranges from 3:1 to 1:1.

2. The composition according to claim 1, in which the level of anionic cleansing surfactant (i) ranges from 10 to 16% by weight based on the total weight of the composition.

3. The composition according to claim 1, in which the polymeric shell of the microcapsule (iii) is an aminoplast resin selected from melamine glyoxal and polyurea.

4. The composition according to claim 1, in which the benefit agent of the core of the microcapsule (iii) is selected from perfumes.

5. The composition according to claim 1, in which the acrylamidopropyltrimonium chloride/acrylamide copolymer (b) has an average molecular weight in the range 800,000 to 1.5 million g/mol and a charge density ranging from 1.5 to 2.2 meq/g.

* * * * *